United States Patent [19]
Ono et al.

[11] Patent Number: 6,036,856
[45] Date of Patent: Mar. 14, 2000

[54] LIQUID CHROMATOGRAPH AND METHOD OF OUTPUTTING AN ANALYSIS RESULT OF THE SAME

[75] Inventors: Takayuki Ono; Kiyotoshi Mori, both of Hitachinaka, Japan

[73] Assignee: Hitachi, Ltd., Tokyo, Japan

[21] Appl. No.: 09/257,617

[22] Filed: Feb. 25, 1999

[30] Foreign Application Priority Data

Feb. 26, 1998 [JP] Japan .................................. 10-044857

[51] Int. Cl.$^7$ .................................................. B01D 15/08
[52] U.S. Cl. ........................................ 210/198.2; 210/656
[58] Field of Search .................................. 210/656, 659, 210/96.1, 101, 198.2; 422/70; 436/161; 703/23, 30, 32; 73/61.52

[56] References Cited

U.S. PATENT DOCUMENTS

| | | | |
|---|---|---|---|
| 4,468,742 | 8/1984 | Jenden | 364/497 |
| 4,719,017 | 1/1988 | Uchino | 210/656 |
| 5,039,409 | 8/1991 | Blaffert | 210/198.2 |
| 5,203,992 | 4/1993 | Drouen | 210/198.2 |
| 5,668,735 | 9/1997 | Dominguez | 702/31 |
| 5,755,559 | 5/1998 | Allington | 210/198.2 |
| 5,804,142 | 9/1998 | Ito | 210/198.2 |
| 5,830,353 | 11/1998 | Henderson | 210/198.2 |
| 5,938,931 | 8/1999 | Ono | 210/198.2 |

*Primary Examiner*—Ernest G. Therkorn
*Attorney, Agent, or Firm*—Kenyon & Kenyon

[57] ABSTRACT

The present invention provides a liquid chromatograph which can easily edit an output format so that an analyst easily use an output of the liquid chromatograph for analysis. In more detail, the chromatograph comprising a chromatographic unit composed of a detector for collecting chromatographic data, an automatic sampler for sampling a sample, a pump for performing eluent switching and liquid transmission and a column oven for keeping a column at a constant temperature; and a data processing means for performing data processing such as waveform processing or quantitative calculation, wherein the data processing means comprises a setting means for arbitrarily setting an output format when an analysis result is output after measurement.

6 Claims, 6 Drawing Sheets

ANALYSIS REPORT : ×××××

NAME OF ANALYST : ×××××
DATE OF CREATION : ×××××
DATE OF ANALYSIS : ×××××
NAME OF SAMPLE : ×××××
VIAL : ×××××
AMOUNT OF INJECTION : ×××××
NUMBER OF INJECTIONS : ×××××

| RT ××× | NAME OF COMPONENT ×××× | NUMBER OF THEORETICAL PLATES ×××× | S/N ××× |

[OK] [CANCEL]

FIG.6

NUMBER OF THEORETICAL PLATES

PROMPT | DATA

| NUMBER OF THEORETICAL PLATES | ⬇ |
| THEOROTICAL DATA | ⬆ |
| THEORETICAL INDEX | ⬇ |

NEW REGISTRATION

[OK] [CANCEL]

FIG.10

# LIQUID CHROMATOGRAPH AND METHOD OF OUTPUTTING AN ANALYSIS RESULT OF THE SAME

BACKGROUND OF THE INVENTION

The present invention relates to a chromatograph and particularly to an editing of an output format of an analysis result of a chromatograph.

A data processor of a liquid chromatograph has a function to adapt an analysis result to a certain format, and to output it by displaying it on a display or the like as a report or by printing it using a printer or the like.

In a conventional data processor of a liquid chromatograph, the format used at outputting the analysis result such as item names used for expressing an output type, an analysis result and an analyzing condition has been specific to each apparatus.

As the item names expressing an analysis result used in the output format, there are various unified standards such as JIS (Japanese Industrial Standards), Japanese Pharmacopoeia, US Pharmacopoeia and the like. Since an item name is different depending on the standard, there are a plurality of names.

The conventional data processor of the liquid chromatograph has an output format specific to each apparatus as described above, and accordingly the item names are also specific to the apparatus. The name cannot be changed even if an analyst wants to use an item name in a different standard or a special name which he daily uses.

Further, since equations for calculating analysis results are also fixed, the calculating equations cannot be changed.

SUMMARY OF THE INVENTION

An object of the present invention is to provide a liquid chromatograph which can easily edit an output format so that an analyst easily uses outputs of the apparatus for analysis.

In order to attain the above-mentioned object, the present invention is characterized by a chromatograph comprising a chromatographic unit composed of a detector for collecting chromatographic data, an automatic sampler for sampling a sample, a pump for switching and transferring an eluent and a column oven for keeping a column at a constant temperature; and a data processing means for performing data processing such as waveform processing or quantitative calculation, wherein the data processing means comprises a setting means for arbitrarily setting an output format when an analysis result is output after measurement.

Further, the present invention is characterized by that in an analysis result of a chromatograph comprising a chromatographic unit composed of a pump for switching and transferring an eluent, an automatic sampler for sampling a sample, a column oven having a column and keeping the column at a constant temperature and a detector for collecting chromatographic data of a sample separated by said column; and a data processing unit for performing data processing such as waveform processing or quantitative calculation, user identification information is input at starting up the data processing unit; each of components composing the chromatographic unit used for measurement being selectively set after inputting the normal identification information; an output format to be output after completion of analysis being set; then the measurement being performed; an analysis result being output based on the set display format.

According to the present invention, by the above-mentioned configuration, an output format to be output after completion of analysis can be set in advance and with easy operation, and an output format depending on an analyst can be output as a report.

DESCRIPTION OF THE PREFERRED EMBODIMENTS

An embodiment of the present invention will be described below, referring to the accompanied drawings.

Figure 3:
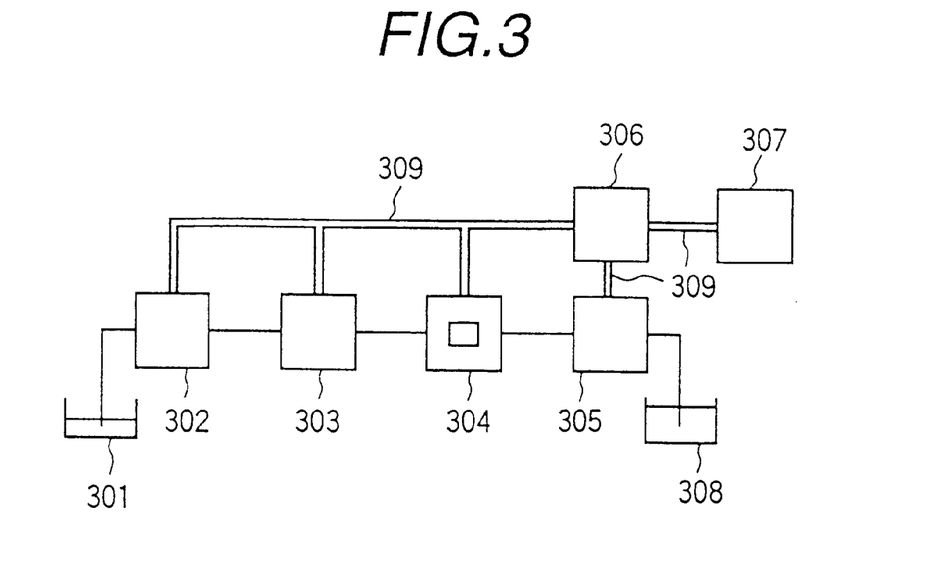
FIG. 3 is a block diagram showing the configuration of a liquid chromatograph.

The configuration of a liquid chromatograph will be described first, referring to FIG. 3. The reference character 301 indicates an eluent, the reference character 302 indicates a pimp, the reference character 303 indicates an automatic sampler, the reference character 304 indicates a column oven and the reference character 305 indicates a detector. The reference character 306 indicates a data processing unit which also controls each of the components (302–305) composing the chromatographic units. The reference character 307 indicates an output unit such as a display or a printer, and the reference character 307 indicates a communication line.

In the above-mentioned configuration, the liquid chromatograph is mainly operated as follows.

A sample injected by the automatic sampler 303 is transferred to the column together with the eluent 301 by the pump 302. The transferred sample is separated into constituents by the column kept at a constant temperature by the column oven 304. The constituents passed through the detector 305 are data-processed by the data processing unit 306.

The process in the liquid chromatograph in accordance with the present invention will be described below in detail, referring to FIG. 1 to FIG. 10.

Figure 1:
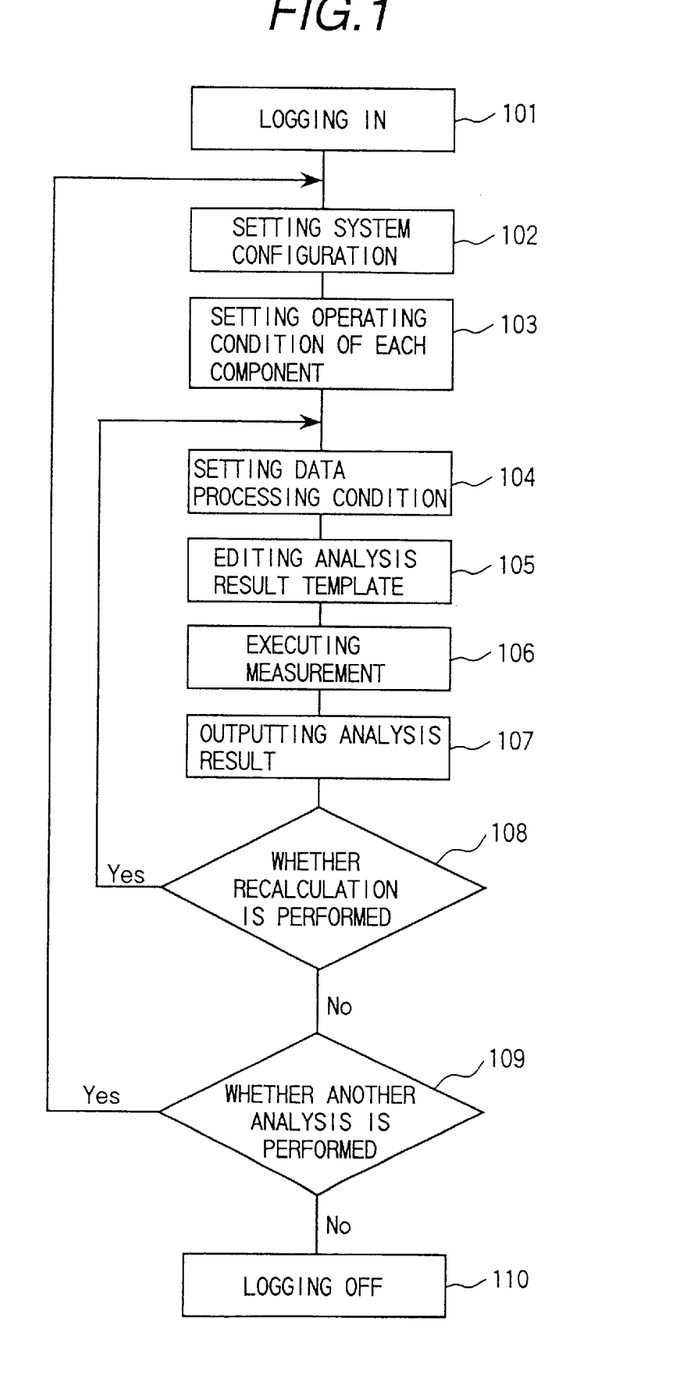
FIG. 1 is a flowchart showing the operation of a data processing unit portion in accordance with the present invention.

FIG. 1 is a flowchart showing the processing in the data processing unit.

Step 101: Initially, an analyst logs on, that is, inputs his user ID and a password to the data processing unit 306 of one component composing the liquid chromatograph.

Therein, if the password is different from that corresponding to the user ID, the data processing unit 306 cannot be operated. The user ID and the password have been preset by an information manager, and the user ID and the password are codes which have been given by the information manager to only users who are allowed to use the data processing unit. The user ID and the password information corresponding to the user ID have been registered in the data processing unit 306 as user management information, and the user management information has been also added with information indicating possession of right to define calculation equations of the data processing. The user management information has a structure shown in FIG. 2. That is, when the logging-on operation is performed, the used management information is queried and then the data processing function can be used only when the input user ID has been registered in the user management information and the input password agrees with the password registered in the used management information. As described above, the user ID and the password are a judging measure for allowing using the data processing unit 306 and a discriminating measure for the right to define the calculation equations used in the data processing.

Stem 102: Before starting measurement, the analyst generating a system configuration file by selecting and inputting each of components of the chromatographic unit composing the liquid chromatograph into the data processing unit 306. The chromatographic unit composing the liquid chromatograph is composed of, for example, the pump 302, the automatic sampler 303, the column oven 304 and the detector 305, as shown in FIG. 3.

Figure 2:
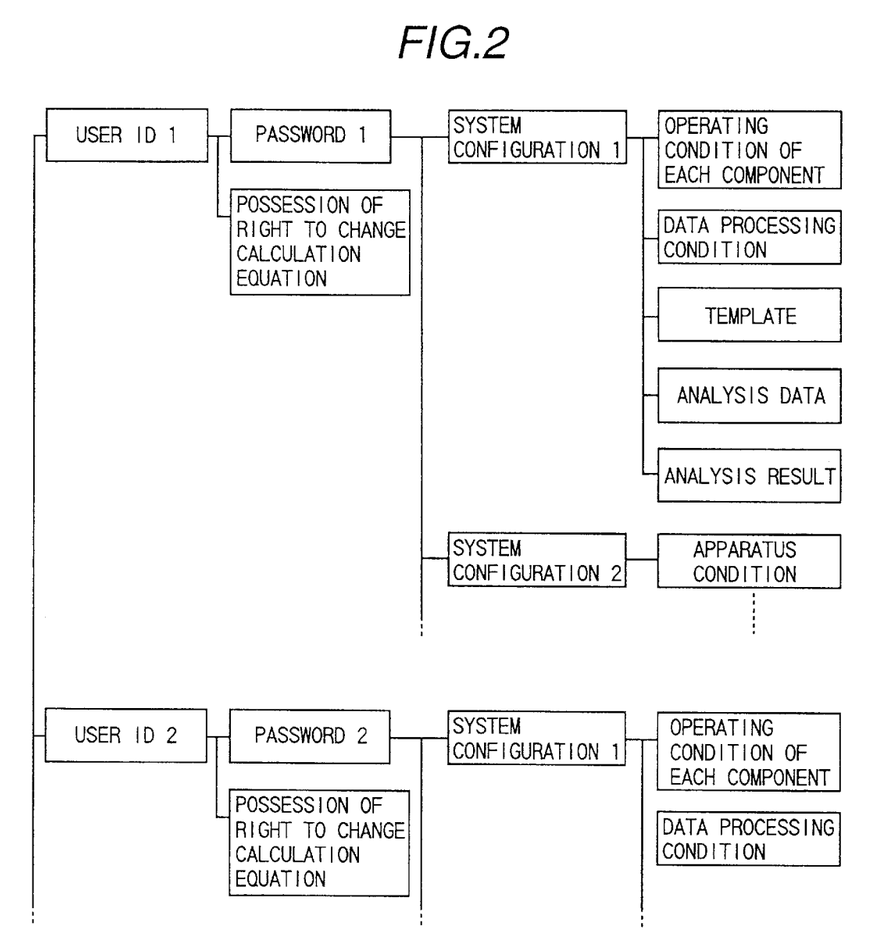
FIG. 2 is a diagram showing a file configuration on a memory of a data processing unit.

Step 103: The analyst generates an analysis condition by inputting an operating condition of each the components composing the chromatographic unit. For example, the operating condition of each of the components composing the chromatographic unit includes an amount of injection and number of injections of the automatic sampler; a mixing ratio of the eluent, a flow rate and an upper and a lower pressure limits of the pump; a temperature set value, and an upper and a lower temperature limits of the column oven; a measuring wavelength, and a measuring time of the detector. The operating condition of each of the components and a data processing condition generated by the analyst are stored together with the system configuration file generated in Step 102 and the user ID and the password, as shown in FIG. 2. That is, analysis conditions having a system configuration similar to each other are stored under the same directory.

Step 104: Next, the analyst generates a data processing condition by inputting a method of quantitatively calculating the analysis data into the data processing unit 306. The operating condition of each of the components and the data processing condition generated by the analyst are stored under the directory of the system configuration file generated in Step 102. That is, analysis conditions having a system configuration similar to each other are stored under the same directory.

Figure 4:
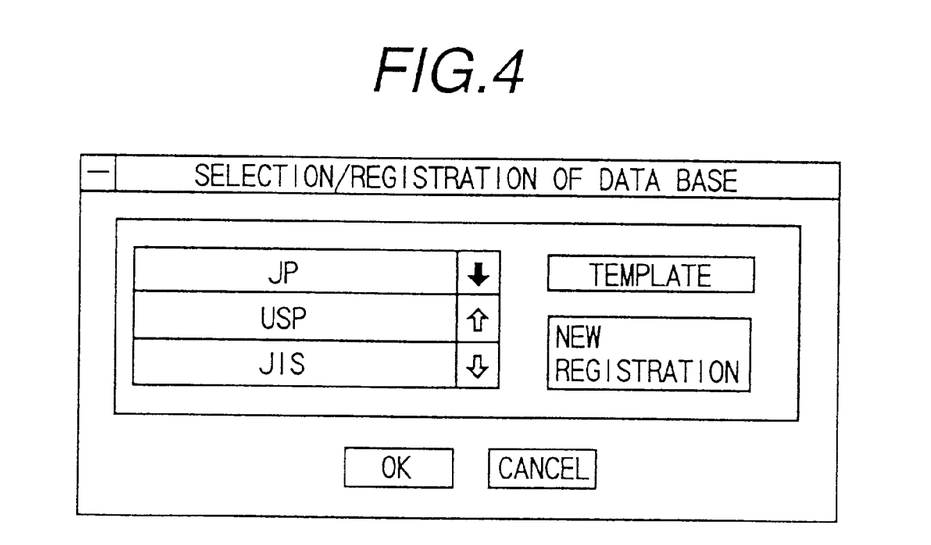
FIG. 4 is a view showing an example of a selecting/registering window for data base.

Step 105: Next, the analyst edits a template for determining an output format of the analysis result. In the output unit 307, a window, shown in FIG. 4, for determining the output format of the analysis result is displayed. In FIG. 4, a column indicating a database name of "JP (Japanese Pharmacopoeia)" is displayed, and columns of "USP (US Pharmacopoeia)". When a portion marked by "↓" in the right end of the column is clicked, columns of "JIS (Japanese Industrial Standards)" are displayed as pull-down menus as shown in FIG. 4. Although the two pull-down menus are displayed here, other database names may be displayed by clicking an arrow portion in the right end of each of the columns to scroll pull-down menus.

Further, the data processing unit 306 of the present embodiment is provided with a glossary of terms (including data such as calculation equations) for each of the standards such as "Japanese Pharmacopoeia", "Japanese Industrial Standards" and "US pharmacopoeia" as a database in advance. In the window for determining the output format of the analysis result shown in FIG. 4, the analyst may select one as terms used in the analysis result out of "Japanese Pharmacopoeia", "Japanese Industrial Standards", "us pharmacopoeia" and so on pre-registered as the database in advance. By this selection, the terms selected by the analyst are used in the output format output as the analysis result.

Furthermore, even once the analyst select the terms used in the analysis result, each of items output as the analysis result may be re-edited. This can be performed, for example, as the following procedure.

Figure 5:
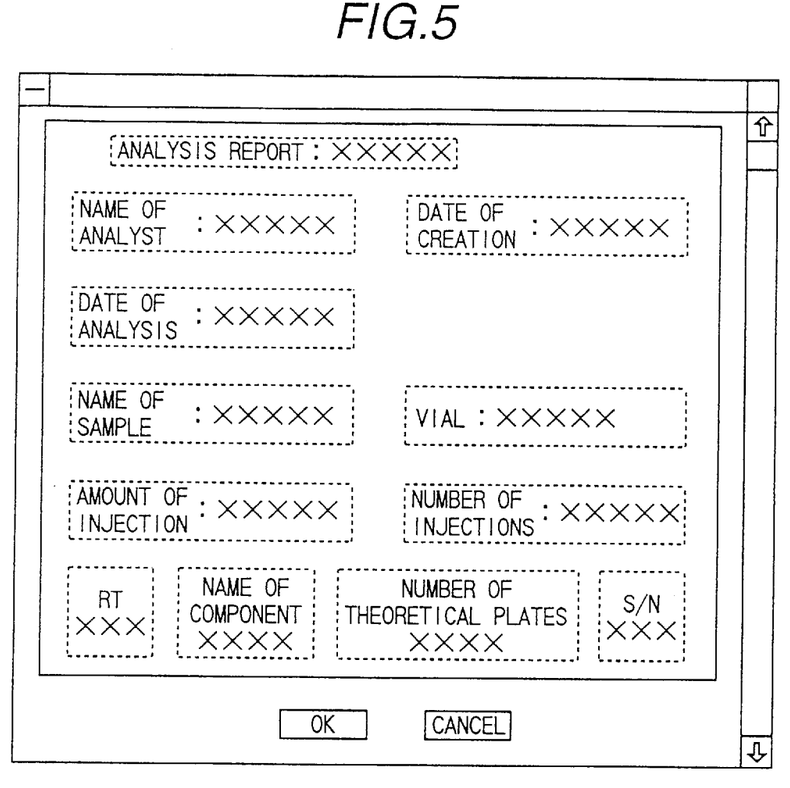
FIG. 5 is a view showing an example of a template window for analysis result.

Initially, the analyst clicks a button of "template" in the window of FIG. 4 to display a template for output format to be output as the analysis result. FIG. 5 shows an example of a template.

Figure 6:
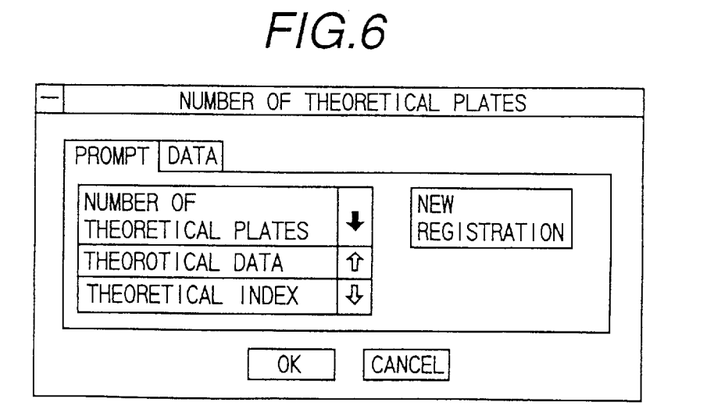
FIG. 6 is a view showing an example of an editing window for items output to an analysis result.

Here, description will be made, for example, on a case of editing an item name of a "number of theoretical plates" which is one item of the analysis result. Initially, a cursor is moved to a column of a "number of theoretical plates" to be clicked to display a small editing window as shown in FIG. 6 and to switch to an editing mode for the "number of theoretical plates". In the case of number of theoretical plates, an output format of the number of theoretical plates as well as the item name may be edited by the small window because of the characteristic of the item.

The small editing window may be also displayed by similarly performing clicking in the other items instead of the "number of theoretical plates", and it is possible to edit an item name and to edit data so as to be matched with the characteristic of the item.

As shown in FIG. 6, editing of an item name is performed by selecting a desired name out of a menu displaying names. By including a term used in a glossary of terms which is selected by the analyst as the initial value, a corresponding term of another glossary of terms stored in the database is usually displayed in the menu as a candidate.

Figure 7:
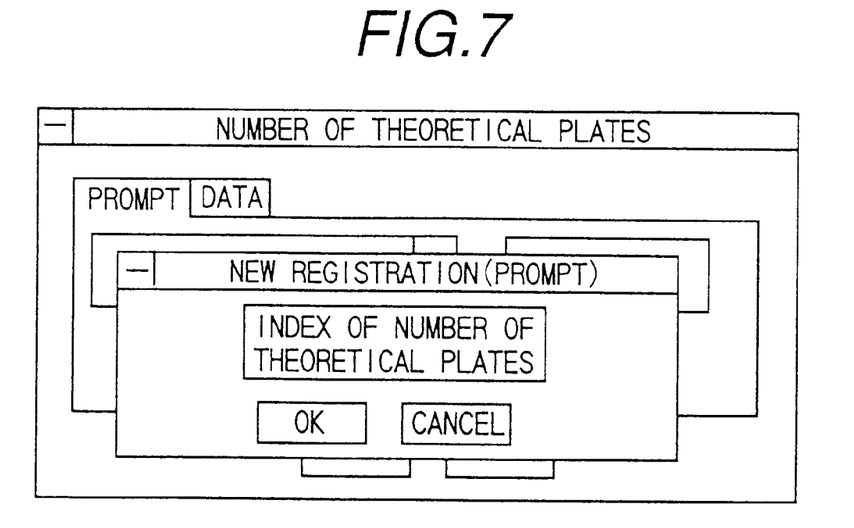
FIG. 7 is a view showing an example of a name registering window for items output to an analysis result.

However, the term may be further edited by the analyst. For example, in a case where a term specific to he analyst himself other than a plurality of registered terms, the new term can be registered by pushing a button "new registration". When the button "new registration" is pushed, a small window for new registration is newly displayed, as shown in FIG. 7. The analyst inputs a term to be newly registered into a column in the displayed small window, and then pushes an OK button. Thus, the newly registered term is added to the menu displaying the name, and the targeting item name can be used for the output format of the analysis result by selecting the new term.

Figure 8:
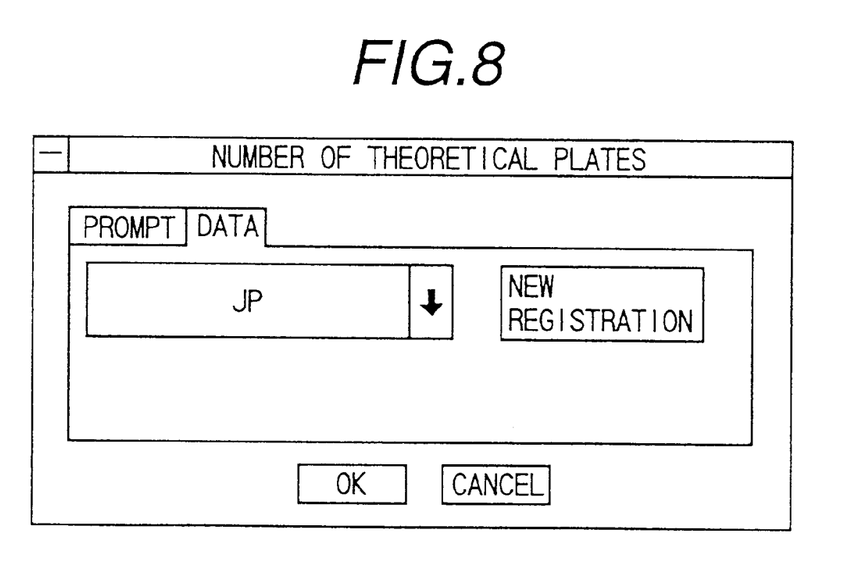
FIG. 8 is a view showing an example of a data editing window for items output to an analysis result.

In editing of the "number of theoretical plates", it is possible to edit edition of a data format, as described above. FIG. 8 shows a small editing window at editing a data format. Since an equation for calculating number of theoretical plates is defined one-to-one correspondingly to each of the standards as follows, the calculation equation can be defined by selecting one out of the standards, "JP (Japanese Pharmacopoeia)", "USP (US pharmacopoeia)" and "EUP (European Pharmacopoeia)".

Examples of calculation equations for the number of theoretical plates (N)

(1) Equation for the Japanese Pharmacopoeia $$N=5.55\ (RT/W_{1/2})^2$$

(2) Equation for the US Pharmacopoeia $$N=16\ (RT/W)^2$$

(3) Equation for the European Pharmacopoeia $$N=5.54\ (RT/W_{1/2})^2$$

where RT is the retention time of peak, W is the base width of peak and $W_{1/2}$ is the half value width.

Although an equation automatically set is the calculation equation of the standard corresponding to a glossary of terms which is selected as the initial value by the analyst, the automatically set equation may be changed to any calculation equation for another standard by the small editing window of FIG. 8.

However, if the analyst is not an ordinary user but a user possessing the right to change the calculation equation for an item outputting the analysis result, that is, a user possessing the right to define the calculation equation for the data processing as described in Step 101, he may select the button "new registration" shown in FIG. 8. When the ordinary user logs in to the data processing unit, the button "new registration" is in blurred display and he cannot not select the button.

Figure 9:
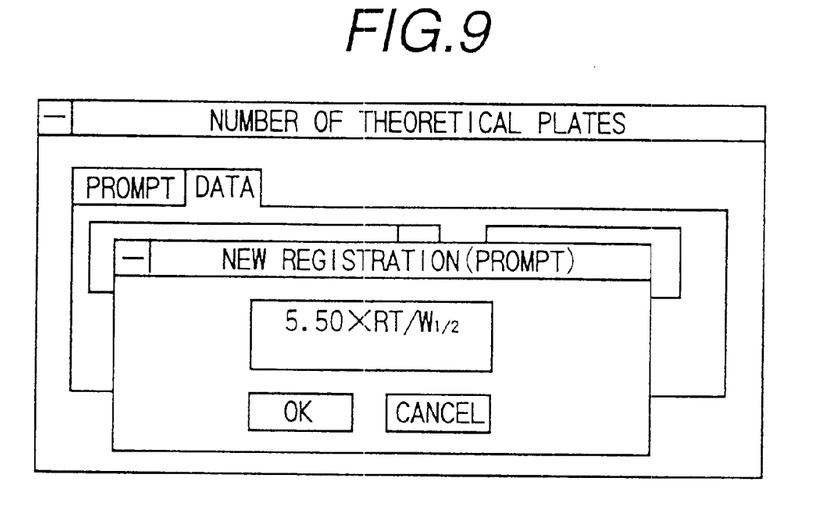
FIG. 9 is a view showing an example of a calculation equation registering window for items output to an analysis result.

When the analyst possessing the right to change the calculation equation for an item outputting the analysis result select the button "new registration", a small widow shown in FIG. 9 is displayed. The analyst can register a specific calculation equation by defining a name of a new calculation equation and the calculation equation corresponding to the name into the input column and selecting the button "OK".

Template editing is performed by repeating the above-described operation for each of the items.

Of course, the editing on each of the items described above is unnecessary when the analyst uses a glossary of terms for the database as it is which is selected before the template editing.

After determining each item name for outputting the analysis result and the data calculation equation is completed, the processing is returned to the window of FIG. 4.

Figure 10:
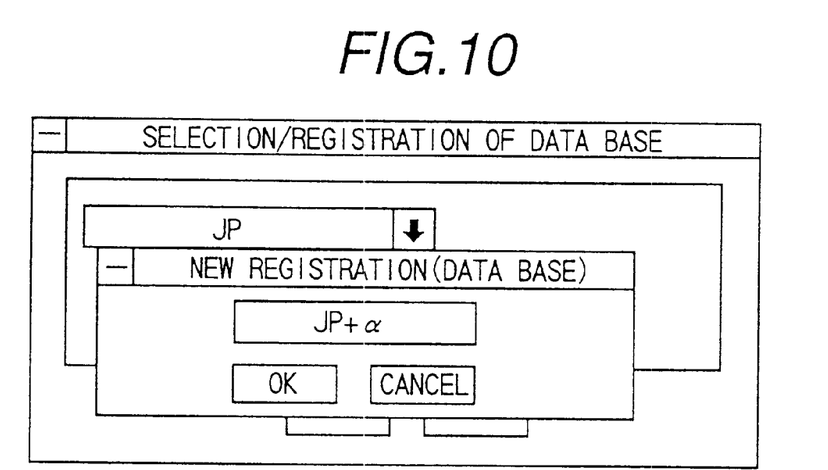
FIG. 10 is a view showing an example of a newly registering window for items output to an analysis result.

Therein, when the contents edited this time is registered as a new database, the new registration button of FIG. 4 is selected to display the small window in FIG. 10, and then a database name is input. Here, the figure shows an example where a name "JP (Japanese Pharmacopoeia) +α" is registered as the data base. By this operation, the contents edited this time can be used from the next time only by designating the database name.

Step 106: The operating condition of each of the components composing the chromatographic unit generated in Step 103 is transmitted to each of the components composing the chromatographic unit through the data processing unit 306. After transmitting the operating condition of each of the components composing the chromatographic unit, the analyst executing measurement to the data processing unit 306. The data processing unit 306 requests each of the components of the chromatographic unit composing the liquid chromatograph to perform measurement operation.

After measurement, the chromatographic data measured according to the operating condition is transmitted to the data processing unit 306. The data processing unit 306 receiving the chromatographic data executes quantitative calculation according to the data processing condition stored in the data processing unit 306. After completing of execution of the quantitative calculation, the analysis data is stored in the memory in the data processing unit 306 together with the analysis result file and the template of format for outputting the analysis result.

Step 107: The analyst outputs the analysis result in a form of report using the output unit 307.

Step 108: In a case where the analysis data is tried to be performed once more after checking the analysis result, that is, where the data processing condition is changed or where the item name output to the analysis result is changed, the processing is returned to Step 104 to reset the data processing condition again.

Step 109: In a case where the re-calculation is not necessary and an analysis of another sample is performed, the processing is returned to Step 102 to reset the system configuration.

Step 110: After completion of all analyses, the analyst logs off to the data processing unit 306.

The following effects can be attained by the present invention.

Since an analyst can easily edit and output an output format of an analysis result in a desired output format using a pre-provided database, it is possible to easily cope with request of analysts in various fields using one analysis system and to improve the analysis efficiency.

Further, since a new item name can be added to an output format of the analysis result when the item name to be output does not exist in the database, it is possible to easily customize the analysis system by the analyst and to flexibly generate the output format.

What is claimed is:

1. A chromatograph comprising a chromatographic unit composed of a detector for collecting chromatographic data, an automatic sampler for sampling a sample, a pump for switching and transferring an eluent and a column oven for keeping a column at a constant temperature; and a data processing means for performing data processing, wherein
said data processing means comprises a setting means for editing or re-editing an output format when an analysis result is output after measurement.

2. A chromatograph according to claim 1, wherein
said data processing means further comprises a plurality of data bases each of which stores a display format used in said output format for each of unified standards; a selecting means for selecting a data base to be formed into a display format out of said plurality of data bases; an output means for converting the analysis result into the display format of the data base selected by said selecting means when the analysis result is output.

3. A chromatograph according to claim 2, wherein
said selecting means comprises a display instructing means for instructing to display the output format, said, output format comprising instructing means comprising a change instruction means for instructing to change content of an item for each displayed item.

4. A chromatograph according to claim 2, wherein said selecting means comprises a newly setting means capable of content of an item for each displayed item, and said database comprises a new registration setting means for storing the content of the item set by said newly setting means and the corresponding displayed item in relation to each other.

5. A chromatograph according to claim 2, wherein said database comprises a calculation equation accumulating means having a plurality of calculation equations used for outputting the number of theoretical plates.

6. A chromatograph according to claim 1, wherein the data processing means comprises waveform processing or quantitative calculation.

* * * * *

UNITED STATES PATENT AND TRADEMARK OFFICE
CERTIFICATE OF CORRECTION

PATENT NO. : 6,036,856
DATED : 14 March 2000
INVENTOR(S) : Takayuki Ono et al.

Page 1 of 3

It is certified that error appears in the above-identified patent and that said Letters Patent is hereby corrected as shown below:

In the Abstract, line 2: After "analyst" insert --can--.

| Column | Line | |
|--------|------|---|
| 2 | 36 | Change "accompanied" to --accompanying--. |
| 3 | 13 | Change "used" to --user--. |
| 3 | 17 | Change "used" to --user--. |
| 3 | 33 | After "each" insert --of--. |
| 3 | 39 | Change "limits" to --limit--. |
| 3 | 40 | Change "limits" to --limit--. |
| 4 | 7 | Change "US pharmacopoeia" to --US Pharmacopoeia-- |

UNITED STATES PATENT AND TRADEMARK OFFICE
CERTIFICATE OF CORRECTION

PATENT NO. : 6,036,856
DATED : 14 March 2000
INVENTOR(S) : Takayuki ONO et al.

It is certified that error appears in the above-identified patent and that said Letters Patent is hereby corrected as shown below:

| Column | Line | |
|---|---|---|
| 4 | 10 | Change "one as terms used in the analysis result out of" to --for the analysis result one of the terms from the--. |
| 4 | 11 | Change "us phar-" to --US Phar- --. |
| 4 | 15 | Change "select" to --selects--. |
| 4 | 45 | Change "he" to --the--. |
| 5 | 30 | After "cannot" delete "not". |
| 5 | 35 | Change "select" to --selects--. |
| 5 | 46 | Change "as it is which is selected" to --verbatim, selected--. |
| 5 | 57 | Change "is registered" to --are registered--. |
| 6 | 64 | Change "instructing" to --giving instructions--; after "said" delete ",". |

UNITED STATES PATENT AND TRADEMARK OFFICE
CERTIFICATE OF CORRECTION

PATENT NO. : 6,036,856
DATED : 14 March 2000
INVENTOR(S) : Takayuki ONO et al.

It is certified that error appears in the above-identified patent and that said Letters Patent is hereby corrected as shown below:

| Column | Line | |
|---|---|---|
| 6 | 66 | Change "instructing" to --giving instructions--. |
| 7 | 2 | Delete "newly". |
| 7 | 3 | After "capable of" insert --editing or re-editing the--. |
| 7 | 7 | Delete "newly". |

Signed and Sealed this

Twenty-ninth Day of May, 2001

Attest:

NICHOLAS P. GODICI

*Attesting Officer*     Acting Director of the United States Patent and Trademark Office